… … …

United States Patent [19]
McDonald et al.

[11] Patent Number: 5,314,243
[45] Date of Patent: May 24, 1994

[54] PORTABLE NURSING CENTER

[75] Inventors: Sean C. McDonald; Robert H. McDonald, both of Pittsburgh; Richard R. Lunak, Fair Oaks; Aldo Zini, Pittsburgh, all of Pa.

[73] Assignee: Automated Healthcare, Inc., Pittsburgh, Pa.

[21] Appl. No.: 986,042

[22] Filed: Dec. 4, 1992

[51] Int. Cl.$^5$ .............................................. E05B 65/00
[52] U.S. Cl. ................................ 312/215; 312/249.11; 221/2
[58] Field of Search ............... 312/215, 249.8, 249.1, 312/249.11, 249.12; 221/2, 9, 92

[56] References Cited

U.S. PATENT DOCUMENTS

| 3,762,601 | 10/1973 | McLaughlin | 221/2 |
| 4,267,942 | 5/1981 | Wick, Jr. et al. | 221/2 |
| 4,635,053 | 1/1987 | Banks et al. | 340/825.31 |
| 4,695,954 | 9/1987 | Rose et al. | 364/413 |
| 4,733,362 | 3/1988 | Haraguchi | 364/479 |
| 4,785,969 | 11/1988 | McLaughlin | 221/2 |
| 4,812,985 | 3/1989 | Hambrick et al. | 364/478 |
| 4,847,764 | 7/1989 | Halvorson | 364/413.02 |
| 4,853,521 | 8/1989 | Claeys et al. | 235/375 |
| 4,857,713 | 8/1989 | Brown | 235/375 |
| 4,896,024 | 1/1990 | Morello et al. | 235/381 |
| 5,014,875 | 5/1991 | McLaughlin et al. | 221/2 |
| 5,088,586 | 2/1992 | Isobe et al. | 194/205 |

Primary Examiner—Kenneth J. Dorner
Assistant Examiner—Gerald A. Anderson
Attorney, Agent, or Firm—Buchanan Ingersoll

[57] ABSTRACT

A portable nursing center has a plurality of selectively locked patient drawers carried in a housing. Each of said drawers are movable between a given open position and a closed position each drawer sized and configured for holding pharmaceutical items which have been prescribed for a specific patient. At least one on demand drawer is also carried by the housing, movable between an open position and a closed position and being sized and configured to hold pharmaceutical and other nursing items used on an as needed basis. A nurse enters a predetermined access data and other data, causing the unit to selectively unlock the appropriate patient drawer or on demand drawer while maintaining other drawers in a locked condition. Whenever the patient is given medicine or otherwise treated the nurse enters or receives information pertinent to that treatment. The unit has a transmitter/receiver to transmit and receive such patient information.

15 Claims, 4 Drawing Sheets

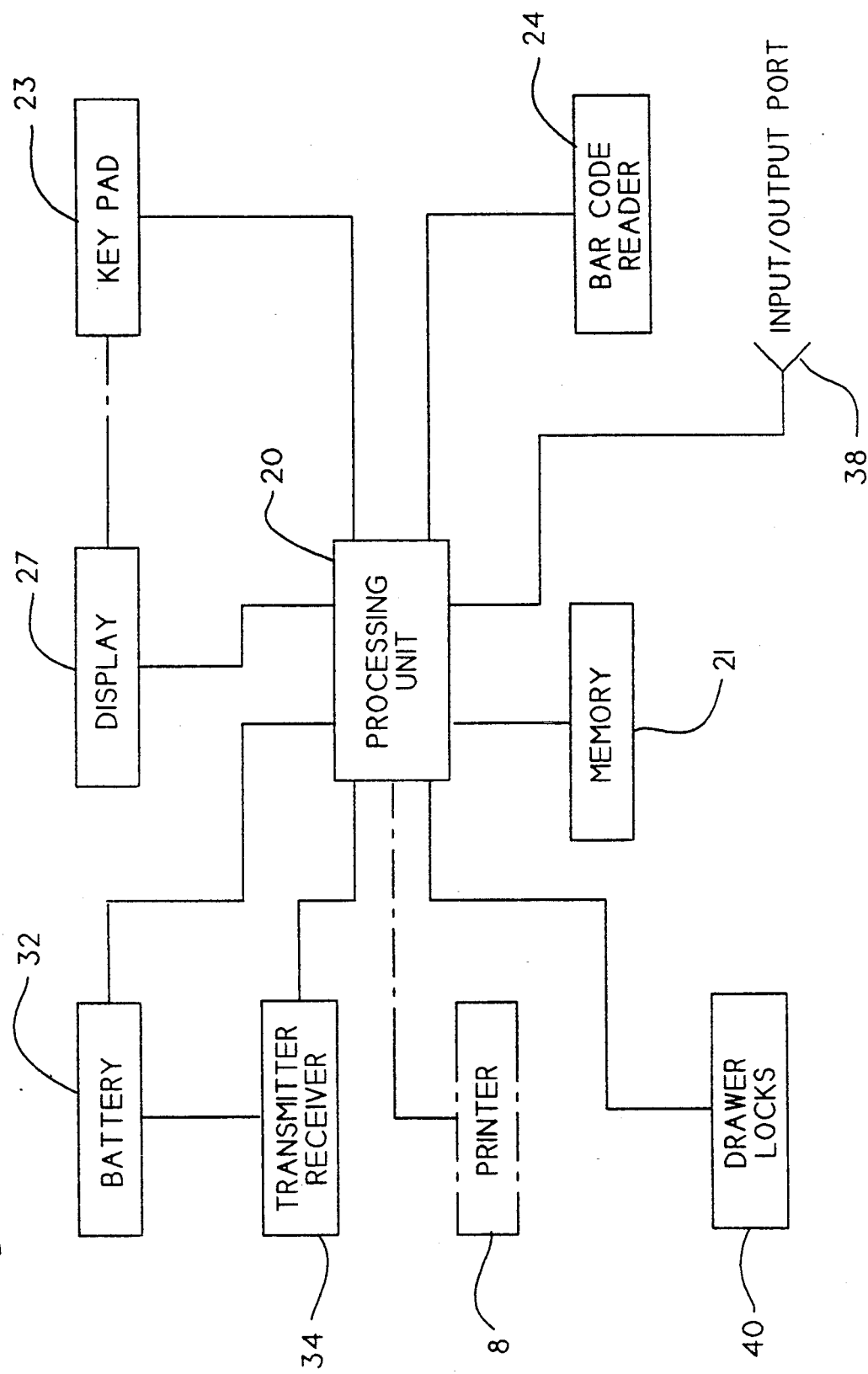

PORTABLE NURSING CENTER

BACKGROUND OF THE INVENTION

The invention generally relates to devices for controlled dispensing of medication and related record keeping in a hospital environment or nursing home or the like.

DESCRIPTION OF THE PRIOR ART

In a hospital environment or the like a large number of pharmaceutical items such as medication, syringes, dressings or bandages are used in the course of individual medical treatment provided to multiple patients. Each patient may receive medications specifically prescribed for him typically to be administered according to a time schedule. The patient may also receive other medications and pharmaceutical items such as aspirin or pain medicine on an as needed basis. In most hospitals, pharmaceutical items are normally stocked in a centralized location in a hospital pharmacy for periodic distribution to nursing stations or the like located throughout the hospital facility. In most hospitals, medication drawers are provided for each patient. Typically, the hospital pharmacy will fill the medication drawers for each of the patients and then transport them to a nursing station located near the patient's room. Usually, several of the drawers are carried on a cart In contrast, on demand drugs are sent to the nursing station separately in response to requests to replenish depleted supplies.

At each nursing station the pharmaceutical items are stored for access by nursing personnel in accordance with individual patient requirements. In this regard, many items are normally maintained in unlocked storage for easy and substantially unrestricted access, while other items such as narcotic medications are normally retained in locked storage to prevent unauthorized access and theft. For all pharmaceutical items, however, withdrawal of pharmaceutical items from inventory is accomplished by updating of the medication administration record (MAR) for the appropriate patient. In this regard, such record maintenance is an important function of nursing personnel to confirm the treatment regimens for each patient, to insure proper charging of the patient accounts, and to permit accurate tracking of the pharmaceutical inventory. Unfortunately, in a typical nursing environment, the medication records are often incomplete and/or inaccurate. As a result the inventory of some or all of the pharmaceutical items is regularly checked, such as at the conclusion of each nursing shift, in an effort to reduce recording and/or treatment errors and further to minimize pilferage losses.

In recent years a variety of devices and systems have been proposed in attempts to provide improved inventory control for pharmaceutical items in a hospital environment or the like. Many such devices have contemplated individual medication dispensers located at bedside in association with individual patients. However, the use of multiple bedside dispensers can be relatively costly and further requires regular manual attention to ensure proper loading and individualized programming for each patient. For some systems, wiring and other major building modifications must be made. Other systems have envisioned centralized units at a nursing station or the like for maintaining different medications and related pharmaceutical items under locked storage. While such centralized units have provided improved safety and enhanced record keeping for narcotic substances, such units have unduly restricted access to many routine pharmaceutical items. They may also require major building modifications for installation. None of these systems are truly portable. Accordingly, prior centralized medication units have not met with commercial acceptance on any significant scale.

Another shortcoming of prior art medication dispensing systems is that they are nonfunctional. They play no role and offer no advantages for other aspects of patient care.

There exists, therefore, a significant need for an improved portable medication dispenser station designed for storage of a wide range of pharmaceutical items which can be relatively easily accessed by authorized personnel in a manner which generates and maintains accurate access records. The present invention fulfills these needs and provides further related advantages.

SUMMARY OF THE INVENTION

We provide an improved nursing station which functions as both a medication dispensing center and a patient information collection center. This nursing station is comprised of a housing having a plurality of patient drawers as well as at least one on demand medication and equipment drawer. A display and data entry means are provided on the housing for viewing and inputting patient information. The data entry means may include a keypad, a bar code reader or a touch screen as well as a data entry port that can be connected to other hospital equipment for entry of data. A transmitter/receiver is provided within the housing for communication with at least one hospital computer. This computer may be in the hospital pharmacy and used for inventory control. It may be the hospital billing computer which tracks medication dispensing for billing purposes. It may also be any other computer which provides or authorizes patient information.

The nursing station is sized so as to fit between the patient beds in a hospital. The top of the nursing station contains a work surface at the proper height and of sufficient size to enable the nurse to perform many of the patient care functions directly on the cart. The nursing center has a modular design which will enable the user to choose a variety of drawer configurations.

A nurse using the system enters an authorized access code in combination with patient information utilizing a keyboard or touch screen. Upon entry of such information the drawer containing the medication prescribed for that patient or the drawer containing on demand medication requested by the patient is unlocked. The drawers are spring loaded so that once unlocked the appropriate drawer will move outward from the housing. The nurse removes and uses the necessary items from the drawer and the unlocked drawer is reclosed and relocked. The processing unit will generate a detailed record specifying the time and date the patient drawer opens, the pharmaceutical items removed, and identification of the nurse or other person accessing the drawer. Preferably, the nurse will be required to answer certain questions relating to the patient identification and items requested from the nursing center. When the drawer is closed the nurse will be asked to confirm the items which have been removed. The collected information is stored in the memory. It can be transmitted to a central computer, printed as paper copy or downloaded at a later time.

The nursing station has a processing unit and memory programmed to enable the nurse to record all types of information that would normally be recorded on the patient chart. Indeed, we prefer to provide a bar code reader and data input/output port which can automatically receive and record information such as the patient's name from his ID bracelet or data from patient monitoring equipment. Therefore, the nursing center becomes the primary focus around which patient care is administered serving as both a location from which to obtain medication as well as a station for input of patient data.

Other objects and advantages of the invention will become apparent from a description of the present preferred embodiments shown in the drawings.

BRIEF DESCRIPTION OF THE FIGURES

FIG. 7 is a block diagram of the data collection and processing equipment which together function as the control unit provided in the nursing center.

DESCRIPTION OF THE PREFERRED EMBODIMENTS

Figure 1:
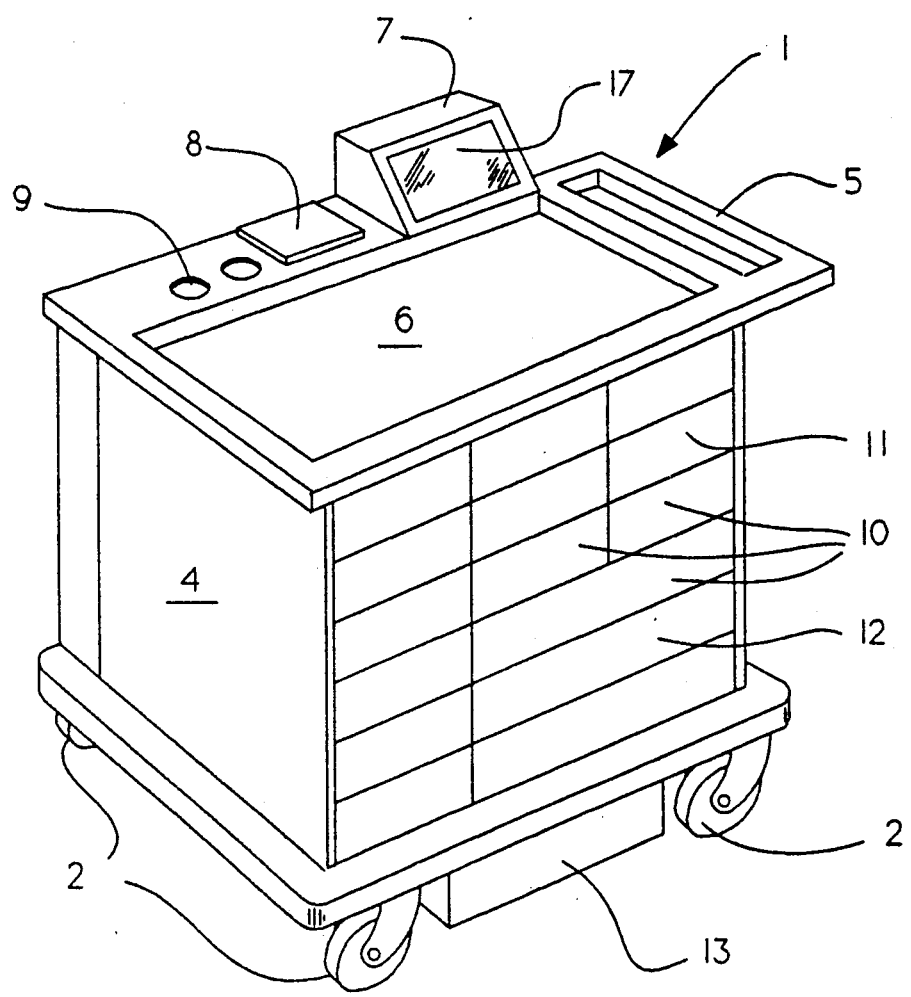
FIG. 1 is a perspective view of a present preferred embodiment of a nursing center.

The nursing center is comprised of a housing or chassis 1 having a front panel 4, a handle 5 at the back, a top work surface 6 and a plurality of drawers 10. Preferably, the drawers are available in two sizes, small individual patient drawers 11 and large drawers 12 to carry on demand drugs and supplies. In the embodiment of FIG. 1 we also provide a large bottom drawer 13. Although the patient drawers 11 and larger drawers 12 are normally locked, the bottom drawer 13 is not.

On top of the chassis 1 we provide a display 7 having a touch screen 17 through which data is entered. We also prefer to provide a printer 8 and storage wells 9 which can hold medication dispensing cups. The chassis is carried on casters 2 and is sized for ease of use. We prefer that the unit be 36 inches long including the handle, 20 inches wide and the top surface be 36 inches from the floor. For such a housing we provide small drawers 11 which are 10 inches wide by 18 inches long by 4 inches deep. Larger drawers 12 are 20 inches wide, 18 inches long and 4 inches deep.

Figure 2:
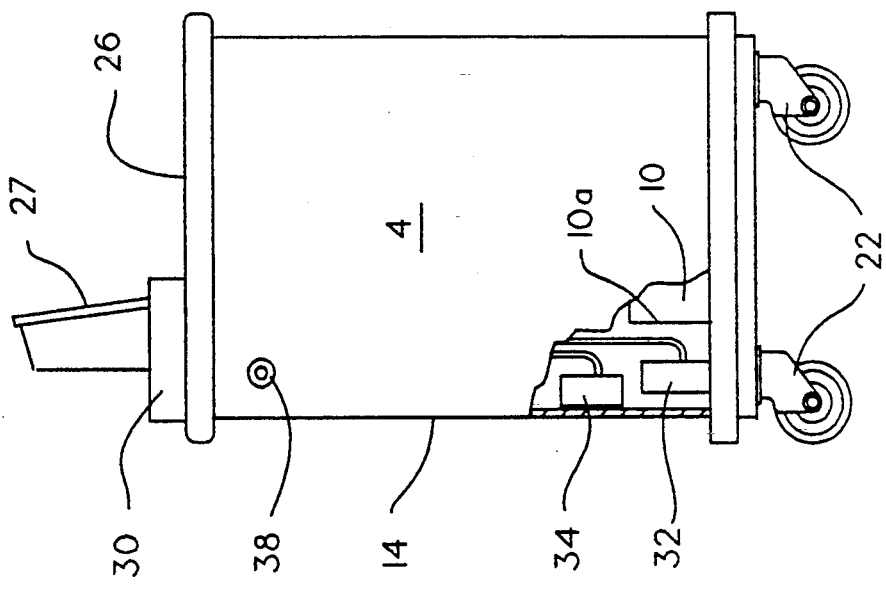
FIG. 2 is a right side view of a second preferred embodiment.
Figure 4:
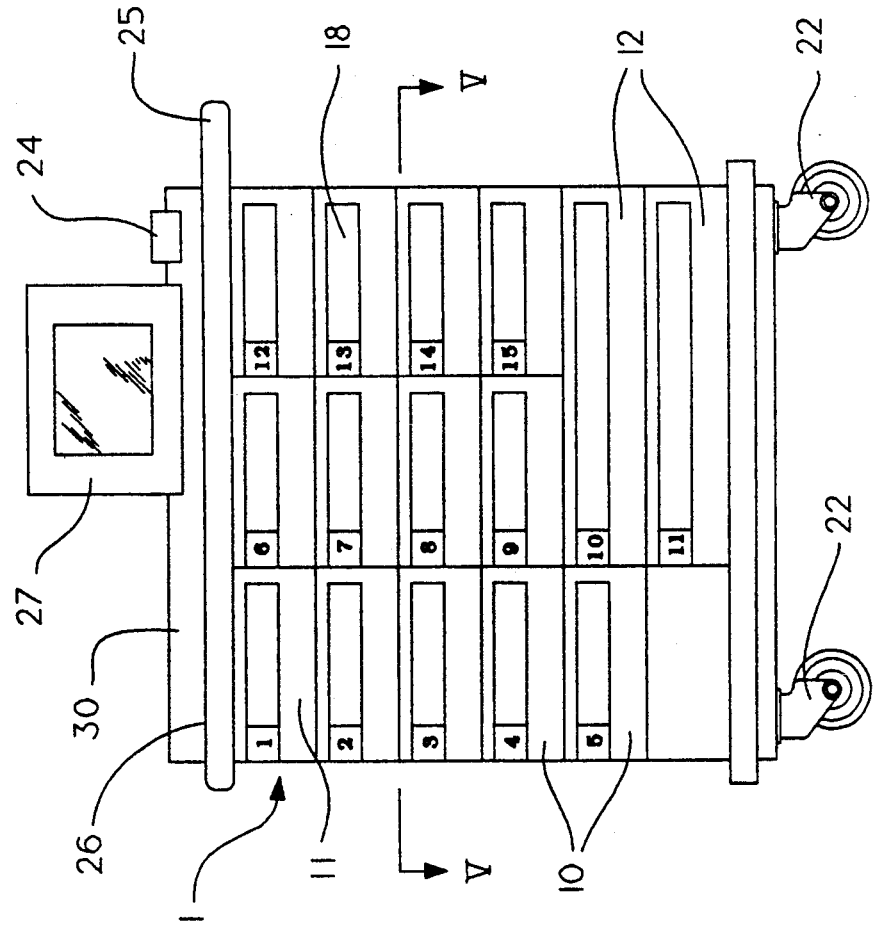
FIG. 4 is a front view partially cut away of the embodiment of FIG. 2.
Figure 3:
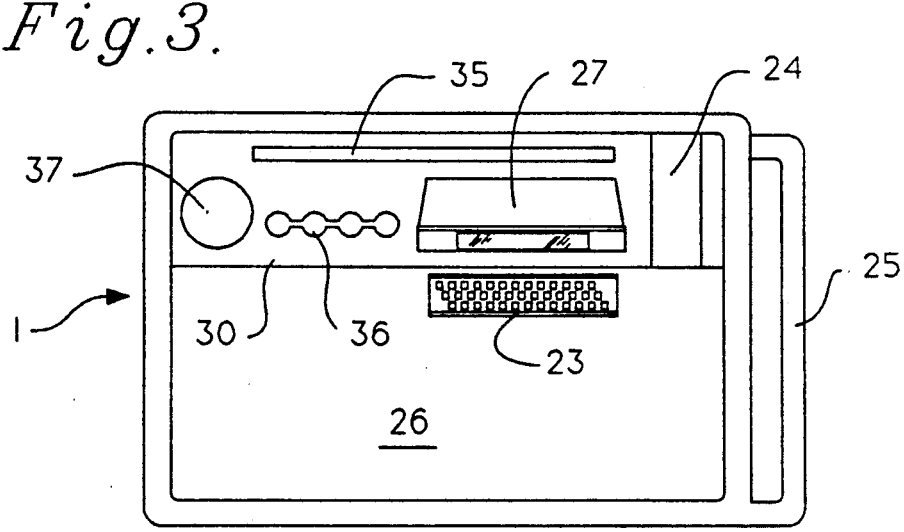
FIG. 3 is a top view of the embodiment of FIG. 2.

A second preferred embodiment is shown in FIGS. 2, 3 and 4. This embodiment is comprised of a chassis 1 having the same dimensions as the embodiment of FIG. 1. In this embodiment the cabinet is mounted on casters 22. A handle 25 is provided adjacent top 26. On the top we provide a display screen 27. Data is entered through keyboard 23 or bar code reader 24. We also prefer to provide an equipment holder 30 on top 26. The equipment holder 30 has a slot 35 sized to hold the base of a clip board. In addition, there is a well 37 for holding cups and connected smaller wells 36 for holding a pen or pencil. As can be seen in FIG. 4 the length of drawer 10 is less than the width of the chassis. Therefore, there is open space between the back 102 of the drawer 10 and the left side 14 of the cabinet 1. Consequently, we are able to provide a battery or set of batteries 32 and a transmitter 34. We also prefer, to provide a data part 38 on the front 4 of the cabinet. This port can be used to input data from hospital monitoring equipment. Alternatively, it can be used to download data into an external computer.

Referring again to FIG. 2 we prefer that each drawer be numbered. We also provide a space 18 on each drawer for entry of a patient name.

Figure 5:
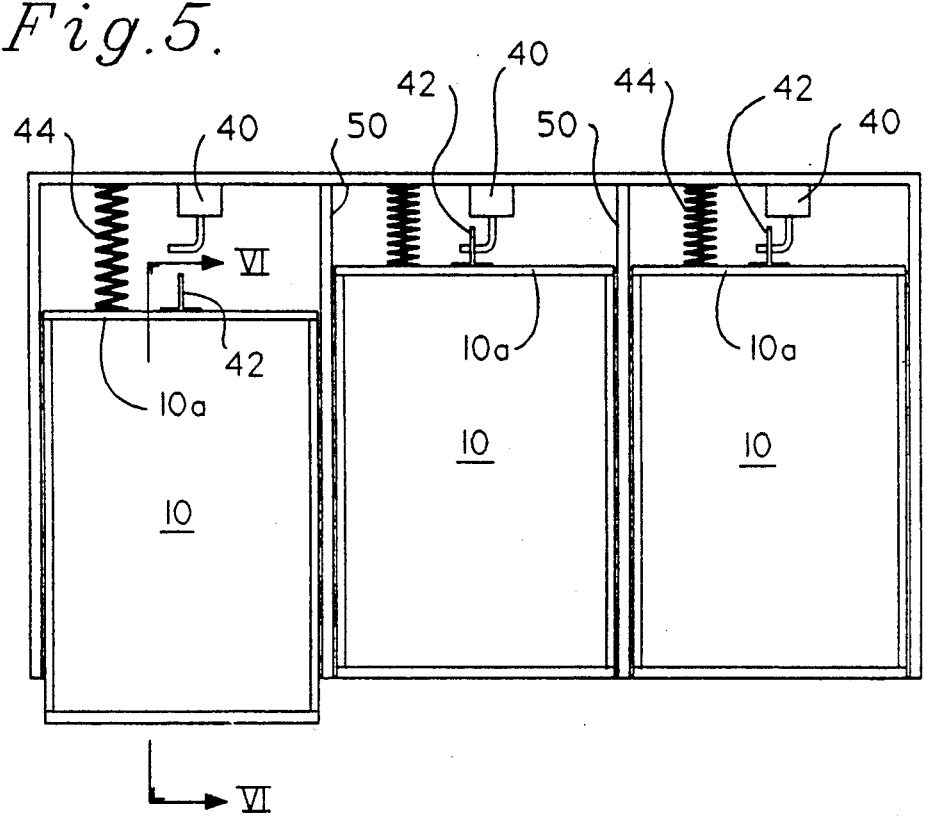
FIG. 5 is a view taken along the lines V—V of FIG. 2.
Figure 6:
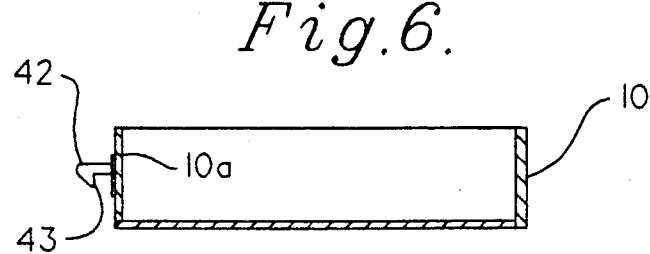
FIG. 6 a view taken along the lines VI—VI of FIG. 5.

Turning now to FIGS. 5 and 6 we provide three drawer locks 40 across each drawer level. Thus, there is one drawer lock for each patient drawer 10. A hook or tab 42 is provided at the back 102 of each drawer 10. Each drawer lock has a hook 41 which engages locking surface 43 of hook 42. Each drawer is spring loaded by spring 44. Thus, when hook 41 is turned away from locking surface 43 springs 44 will push the drawer slightly outward as shown in FIG. 5. We prefer to provide removable dividers 50 between the drawers. Hence, we are able to substitute a larger drawer 12 for two or three smaller drawers 11. The larger drawers will have two or three locks which are engaged by the hooks 41 of door locks 40. Locks 40 can be simple solenoid plungers which turn or retract to unlock the drawer.

The present nursing center is quite durable and easy to use. First, the drawers 11 and 12 are stocked. Normally this will be done on a daily basis in accordance with the schedule established by the pharmacy. The nurse pushes the nursing center to a patient's room near a patient's bedside. She then enters an access code using a computer keyboard, touch screen or bar code reader. Then she identifies the patient to be treated an the medication which is required. The nursing center has been programmed so that in memory 21 there will be an identification of the patients to which each patient drawer 11 corresponds. There will also be information as to what is contained in the larger on demand drawers 12. Thus, when the processing unit sees the patient identification and medication begin requested it will cause a drawer lock 40 to unlock the appropriate patient drawer. The nurse removes the patient medication from the drawings, administrators it to the patient and recloses the drawer. At that point the display will request the nurse to confirm that ht medication has been dispensed to the patient. Upon receiving that information the nursing station may either store the information in memory or transmit it to an external computer through a transmitter/receiver 34. If the information is stored it can be later downloaded through input/output port 36.

The nursing center can also be used to receive information about the patient which is contained in memory or received from transmitter/receiver 34. Thus, after entering an access code and patient information the nurse could enter diagnostic information, view medical history or receive other information which is not required for dispensing medicine. Hence, the nursing center becomes a focal point for patient treatment.

It should be noted that no special wiring is required to be installed for a hospital to use this portable nursing station. The unit is sufficiently large to accommodate drawers for a maximum number of patients normally assigned to one nurse. Hence, our portable nursing station could be assigned to an individual nurse on each shift. The nurse could store her stethoscope, thermometer or other equipment in any of the larger drawers.

Although we have shown present preferred embodiments of our nursing center it should be particularly understood that the invention is not limited thereto, but may be variously embodied within the scope of the following claims.

We claim:

1. A portable nursing center comprising:
   a) a housing having a base and a plurality of wheels attached to the base;
   b) a plurality of patient drawers carried by the housing, each of said drawers being movable between a given position and a closed position each drawer sized and configured for holding pharmaceutical items which have been prescribed for a specific patient;
   c) patient identification means affixed to each patient drawer;
   d) at least one on demand drawer carried by the housing, movable between an open position and a closed position and being sized and configured to hold pharmaceutical and other nursing items used on an as needed basis;
   e) a control unit for selectively locking said patient drawers and at least one on demand medication drawer to prevent access thereto, said control unit including data entry means for entry of predetermined access data and other data, lock means for selectively locking and unlocking said patient drawers and on demand medication drawers and a processing unit with an associated memory for unlocking selected drawers in response to entry of access data while maintaining other drawers in a locked condition and recording at least a portion of the access data; and
   f) a transmitter connected to the central unit for transmitting selected access data and other data from the medication dispensing center to a remote receiver, the nursing center being sized and constructed so that when filled with pharmaceuticals and other nursing items, the nursing center can be moved through a nursing area by a single nurse.

2. The nursing center of claim 1 also comprising at least one removable partition positioned between adjacent drawers.

3. The nursing center of claim 2 wherein the at least one removable partition is sized and positioned to permit one larger drawer to be substituted for at least two smaller drawers when the removable partition is removed.

4. The nursing center of claim 1 wherein the control unit includes a memory and a processing unit, the memory containing a program which permits only authorized users to enter data and remove selected pharmaceuticals from the nursing center.

5. The nursing center of claim 1 also comprising a receiver connected to the control unit.

6. The nursing center of claim 1 also comprising a writing surface sized and positioned to be used by a care-giver to record information about patient care.

7. The nursing center of claim 1 also comprising a touch screen connected to the control unit.

8. The nursing center of claim 1 wherein the data entry means is at least one of a keyboard and a bar code reader.

9. The nursing center of claim 1 also comprising a display connected to the control unit.

10. The nursing center of claim 9 wherein the display may also function as a touch screen.

11. The nursing center of claim 1 also comprising a printer connected to the control unit.

12. The nursing center of claim 1 also comprising an equipment holder attached to the housing.

13. The nursing center of claim 1 also comprising at least one spring attached to at least one patient drawer, the spring being sized and positioned to bias the patient drawer to extend from the housing when the patient drawer is unlocked.

14. The nursing center of claim 1 wherein the housing contains a top at least a portion of the top being sized and positioned to serve as a writing surface.

15. The nursing center of claim 1 also comprising a handle attached to the housing.

* * * * *